United States Patent
Mimori et al.

(10) Patent No.: US 8,402,846 B2
(45) Date of Patent: Mar. 26, 2013

(54) SAMPLE TRITURATION VESSEL, TOOL AND METHOD USING THE SAME

(75) Inventors: Tomohiro Mimori, Sapporo (JP); Kenji Narahara, Ogori (JP)

(73) Assignee: Mizuho Medy Co., Ltd., Saga (JP)

( * ) Notice: Subject to any disclaimer, the term of this patent is extended or adjusted under 35 U.S.C. 154(b) by 845 days.

(21) Appl. No.: 12/087,679

(22) PCT Filed: Jan. 16, 2007

(86) PCT No.: PCT/JP2007/050481
§ 371 (c)(1),
(2), (4) Date: Oct. 23, 2008

(87) PCT Pub. No.: WO2007/083617
PCT Pub. Date: Jul. 26, 2007

(65) Prior Publication Data
US 2009/0084202 A1    Apr. 2, 2009

(30) Foreign Application Priority Data
Jan. 20, 2006    (JP) .................................. 2006-012526

(51) Int. Cl.
G01N 33/48      (2006.01)
G01N 33/487    (2006.01)
(52) U.S. Cl. ...................................... 73/866; 73/864.91
(58) Field of Classification Search ..................... 73/863, 73/864.91, 866; 241/169
See application file for complete search history.

(56) References Cited

U.S. PATENT DOCUMENTS

| | | | | |
|---|---|---|---|---|
| 3,786,820 A | * | 1/1974 | Kopfer | 132/74.5 |
| 5,330,916 A | * | 7/1994 | Williams et al. | 435/286.4 |
| 5,478,311 A | * | 12/1995 | Klearman | 604/82 |
| 5,731,199 A | * | 3/1998 | Roggero | 435/306.1 |
| 7,735,763 B2 | * | 6/2010 | Bell et al. | 241/169.1 |
| 2006/0078474 A1 | | 4/2006 | Yamamoto et al. | |

FOREIGN PATENT DOCUMENTS

| | | |
|---|---|---|
| JP | 63-112974 | 5/1988 |
| JP | 5-187977 | 7/1993 |
| JP | 3000661 | 6/1994 |
| JP | 9-15123 | 1/1997 |
| JP | 10-090131 | 4/1998 |
| JP | 2003-315223 | 11/2003 |
| JP | 2004-101297 | 4/2004 |
| JP | 2005-246155 | 9/2005 |

OTHER PUBLICATIONS

International Search Report issued Mar. 6, 2007 in the International (PCT) Application PCT/JP2007/050481 of which the present application is the U.S. National Stage.
"Physicochemical Instrument for Research No. 1700" issued in Apr. 2012, by Kenis Limited (with translation).
"Bio Medical Instrument 2005-2007", published by Cosmo Bio Co., Ltd. (with translation).

* cited by examiner

Primary Examiner — Hezron E Williams
Assistant Examiner — Nashmiya Fayyaz
(74) Attorney, Agent, or Firm — Wenderoth, Lind & Ponack, L.L.P.

(57) ABSTRACT

There is provided a sample trituration vessel that even when the sample is relatively hard, enables triturating of the sample easily and with high efficiency. The sample trituration vessel includes a tubular body having an opening at one end and having a bottom part at the other end thereof. The tubular body is furnished with a rugged portion there-inside so as to be able to meet another rugged port formed on a trituration rod. The sample trituration vessel itself can exert shearing effect on the sample. The tubular body is formed of flexible material, and upon application of external force from outside of the tubular body, the tubular body is deformed, thereby breaking down the sample held within the tubular body.

11 Claims, 6 Drawing Sheets

US 8,402,846 B2

SAMPLE TRITURATION VESSEL, TOOL AND METHOD USING THE SAME

BACKGROUND OF THE INVENTION

I. Technical Field

The present invention relates to a sample trituration vessel for triturating an organic sample derived from an animal or a plant therein with high efficiency, and art related thereto. To be more specific, the present invention is suitable for triturating a sample relatively hard (for example, plant-leaves immersed in buffer). In a preferable example, the present invention is suitable for a case where an orange farmer triturates a sample (for example, leaves of an orange) in or near his/her orange field in order to detect whether or not the orange is suffered from a specific disease.

II. Description of the Related Art

The immunochromatography method is frequently used as technology of qualitatively or quantitatively analyzing a substance to be detected in a liquid sample (especially, in an organic ingredient) in view of simple and rapid operation of the method. More concretely, a substance, which is specific to both labeled reagent and the substance to be detected, is arranged at a predetermined zone of a test piece flowably/not flowably. Upon application of a sample to a sample-applying portion provided at the predetermined zone of the test piece, the predetermined (detection) zone is formed such that a sign indicating a detection result will appear thereat.

The inventors of the present invention have technological repertories in the field of detectors according to the immunochromatography method, and have made every effort to develop trituration of samples, which is a portal portion of the detectors. Mainly in technical fields relevant to medical science, biology, or the like, various kinds of trituration methods have been carried out and/or proposed. These trituration methods can be roughly classified as follows.

COMPARATIVE EXAMPLE 1

A sample immersed in buffer is put into a mortar, and the sample is ground with a pestle. This example is widely used in the above-mentioned fields, and there are the following problems.

The diameter of the mortar is usually about 90 mm. When there are many samples, a large space is needed for trituration thereof.

The sample easily tends to be attached to the outer surfaces of the mortar and pestle, thereby increasing loss of the sample. When the sample is very little, fall of detection precision may be caused.

The set of the mortar and pestle is expensive (about 500 Japanese Yen).

COMPARATIVE EXAMPLE 2

A pestle (including a pole, and a conical head furnished there-with) and a vessel utilized for centrifugal separation are used. Since tools are smaller than those of Comparative example 1, this example has advantage because loss of a small quantity of sample is less than that of Comparative example 1. The head of the pestle and the inner surface of the vessel, however, are specular surfaces. Efficiency of trituration is low when the sample is relatively hard (for example, leaves of a plant, or the like).

COMPARATIVE EXAMPLE 3

This is disclosed in Japanese patent application Laid open on No. S63-112974. That is, grooves are formed on a head of a pestle, thereby enabling to improve efficiency of trituration even when a sample is relatively hard. As described in detail later, however, experiments by the inventors prove that the efficiency of trituration according to this example is not enough when the sample is relatively hard.

COMPARATIVE EXAMPLE 4

As disclosed in Japanese patent application Laid open on No. H05-187977 or Japanese patent application Laid open on No. H09-15123, a thin bag made of synthetic resin is prepared, and meshes are formed there-inside. Inspection by the inventors, however, indicates that the bag may be broken according to a condition of pressure when trituration is carried out.

In view of the above, an object of the present invention is to provide a sample trituration vessel that even when the sample is relatively hard, enables triturating the sample easily and with high efficiency.

A first aspect of the present invention provides a sample trituration vessel used for homogenization, comprising: a tubular body including an opening at one end of the tubular body and a bottom part at the other end of the tubular body, wherein a rugged portion is formed on inside of the tubular body.

A second aspect of the present invention provides a trituration vessel as defined in the first aspect, wherein the rugged portion is formed so as to be able to meet another rugged portion formed on a trituration rod.

According to these arrangements, the sample trituration vessel itself can exert shearing effect on the sample, thereby enabling triturating of the sample easily and with high efficiency even when the sample is relatively hard.

A third aspect of the present invention provides a trituration vessel as defined in the first aspect, wherein the tubular body is formed of flexible material, and upon application of external force from outside to the tubular body, the tubular body is deformed, thereby breaking down a sample held within the tubular body.

According to this arrangement, when the sample is put into the tubular body of the trituration vessel and the tubular body is rubbed with fingers from outside, the sample in the tubular body is able to be broken, thereby enabling triturating of the sample with high efficiency even when the sample is relatively hard.

A fourth aspect of the present invention provides a trituration vessel as defined in the first aspect, wherein the rugged portion is composed of a plurality of protrusions.

According to this arrangement, the plurality of protrusions arc is able to come in touch with the sample, thereby enabling triturating of the sample with high efficiency even when the sample is relatively hard.

A fifth aspect of the present invention provides a trituration vessel as defined in the first aspect, wherein the rugged portion forms a shape of stairs to constitute a rough face.

According to this arrangement, the rough face is able to come in touch with the sample, thereby enabling triturating of the sample with high efficiency even when the sample is relatively hard.

A sixth aspect of the present invention provides a trituration vessel as defined in the first aspect, wherein the rugged portion is formed at an inner side of the bottom part.

According to this arrangement, the sample is able to come in touch with the sample while pressing the sample against the bottom part, thereby enabling triturating of the sample with high efficiency even when the sample is relatively hard.

A seventh aspect of the present invention provides a trituration vessel as defined in the first aspect, wherein a conical tapered portion is provided near the bottom part of the tubular body.

Providing the conical tapered portion causes the sample to concentrate near a center of the bottom part when the sample settles down, thereby enabling triturating of the sample with high efficiency even when the sample is relatively hard.

An eighth aspect of the present invention provides a trituration vessel as defined in the seventh aspect, wherein the rugged portion is formed at an inner side of the tapered portion.

According to this arrangement, the mortar-like tapered portion can exert shearing effect on the sample, thereby enabling triturating of the sample with high efficiency even when the sample is relatively hard.

A ninth aspect of the present invention provides a trituration vessel as defined in the first aspect, wherein the tubular portion is formed of transparent or translucent material.

According to this arrangement, an operator can triturate the sample with high efficiency while observing a state of the sample held within the tubular portion from outside of the tubular portion.

A tenth aspect of the present invention provides a sample trituration tool, comprising: the sample trituration vessel as defined in the first aspect; and a trituration rod for being inserted into the sample trituration vessel and further for triturating the sample held within the sample trituration vessel, wherein the trituration rod comprises: a rod body; and a head portion provided at an apical end of the rod body, and wherein another rugged portion that meets the rugged portion of the sample trituration vessel is provided at the head portion.

According to this arrangement, the rugged portion of the sample trituration vessel and the other rugged portion of the trituration rod can pinch the sample with each other to exert shearing effect on the sample. Thereby, the sample is triturated with high efficiency even when the sample is relatively hard.

EFFECT OF INVENTION

According to the present invention, the rugged portion of the sample trituration vessel can exert shearing effect on the sample, thereby enabling triturating of the sample with high efficiency even when the sample is relatively hard.

In addition, the sample trituration vessel has the same excellent portability as that of other detectors according to the immunochromatography method. The sample can be triturated with high efficiency at a spot (for example, immediately near fruit trees with fear of infection, or the like). A detection result with the detector can be obtained. The detection of infection and countermeasures against escalation thereof can be put into practice rapidly and easily. This is very helpful to farmers and persons relating thereto.

BRIEF DESCRIPTION OF THE DRAWINGS

FIG. 5 (*b*) is a longitudinal section of the second rugged portion in Embodiment 2 of the present invention;

DETAILED DESCRIPTION OF THE INVENTION

Embodiment 1

Figure 1:
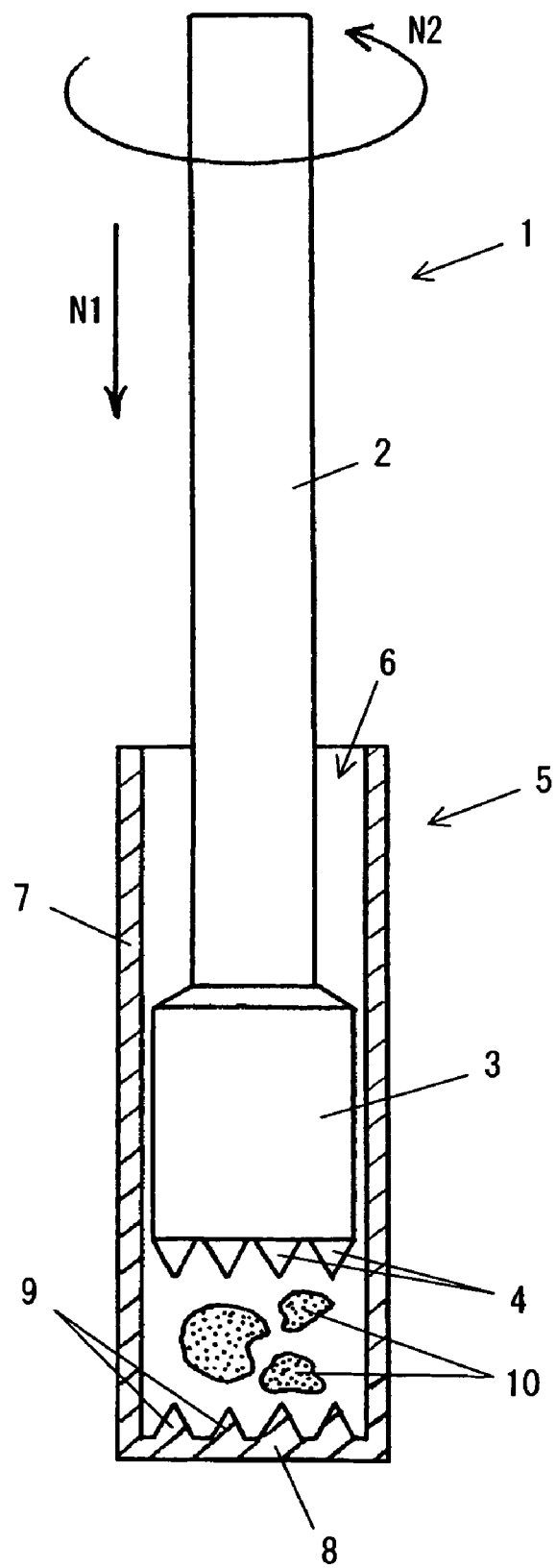
FIG. 1 is a sectional view of a sample trituration vessel in Embodiment 1 of the present invention.

Embodiments of the present invention will now be explained referring to the attached drawings. FIG. 1 is a sectional view of a sample trituration vessel in Embodiment 1 of the present invention.

As illustrated in FIG. 1, a sample trituration tool of Embodiment 1 is equipped with a trituration rod 1 and a sample trituration vessel 5.

The trituration rod 1 comprises: a rod body 2 having a cylindrical and tapered shape; and a head portion 3 provided at a lower end of the rod body 2. A rugged portion 4 is formed at a lower end of the head portion 3. The rugged portion 4 is composed of a plurality of protrusions.

The sample trituration vessel 5 is equipped with a tubular body 7. The tubular body 7 has an opening 6 at an upper end and a bottom part 8 at a lower end, respectively. The tubular body 7 is formed in a manner such that the head portion 3 of the trituration rod 1 can be inserted therein. A rugged portion 9 is formed on an upper surface of the bottom portion 8 upward (that is, meeting the rugged portion 4 of the head portion 3). The rugged portion 9 is composed of a plurality of protrusions like the rugged portion 4.

When a sample 10 is put into the tubular body 7 via the opening 6 and the head portion 3 of the trituration rod 1 is inserted into the tubular body 7 as shown in FIG. 1, the rugged portion 4 and the rugged portion 9 have positional relationship that pinches the sample 10 with each other. In this state, when the rod body 2 is dropped in a direction of arrow N1, the rugged portion 4 presses the sample 10 to break down the sample 10. When the rod body 2 is rotated in a direction of arrow N2 or in reverse, the rugged portion 4 and the rugged portion 9 exert shearing effect on the sample 10. As a result, the sample 10 is triturated with high efficiency even when the sample 10 is relatively hard (for example, leaves of a plant). The well-triturated sample can proceed to the next process (for example, detection process utilizing a detector according to the immunochromatography method).

It is, herein, preferable that the trituration rod 1 and the sample trituration vessel 5 are injection molding products made from synthetic resin. In this way, these elements can be manufactured cheaply and disposable usage thereof can be adopted. These elements can be made stronger than a bag to be hard to be broken.

Embodiment 2

Figure 2:
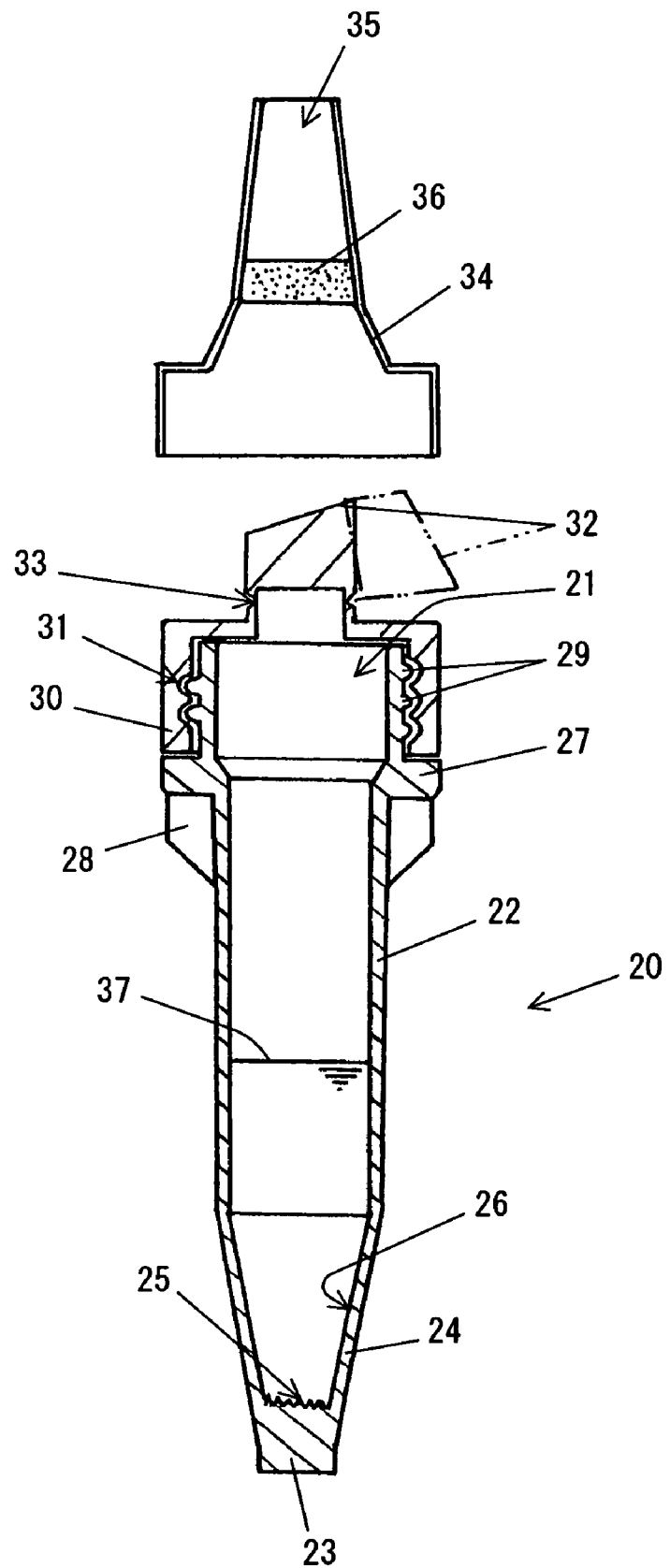
FIG. 2 is a sectional view of a sample trituration vessel in Embodiment 2 of the present invention.
Figure 3:
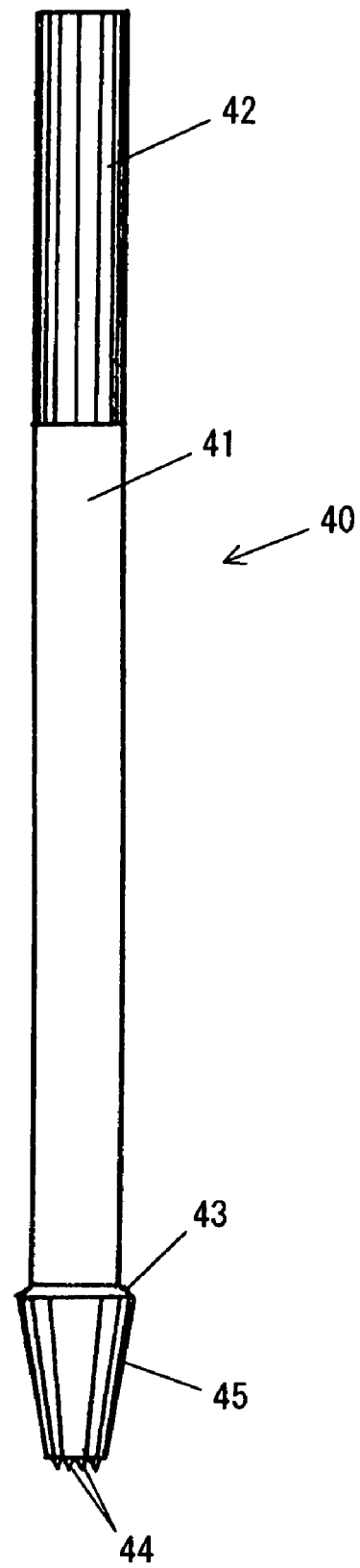
FIG. 3 is a front view of a trituration rod in Embodiment 2 of the present invention.

FIG. 2 is a sectional view of a sample trituration vessel in Embodiment 2 of the present invention, and FIG. 3 is a front view of a trituration rod in the same.

As illustrated in FIG. 3, a trituration rod 40 of this Embodiment is equipped with a cylindrical and tapered rod body 41, and a head portion 43 provided at a lower end of the rod body 41. A first rugged portion 44 is formed at a lower end of the head portion 43. The first rugged portion 44 is composed of a plurality of protrusions. A slanted surface of the head portion 43 has a shape of a cone becoming narrow downward (that is, tapering off). A plenty of grooves are cut on the surface to form a second rugged portion 45. A plurality of vertical grooves arc is cut on an upper part of the rod body 41 to form a gripping part 42. Thereby, a hand of an operator gripping the trituration rod 40 is hard to slip.

As illustrated in FIG. 2, the sample trituration vessel of this Embodiment is equipped with a sample trituration vessel 20, a cap 30, and a nozzle 34.

The sample trituration vessel 20 includes a tubular body 22 having an opening 21 at an upper end and a bottom part 23 at a lower end, respectively. Near the bottom part 23 of the tubular body 22, a tapered portion 24 that has a shape of a cone becoming narrow downward (that is, tapering off) is formed.

The head portion 43 of the trituration rod 40 can be inserted from the opening 21 to the second rugged portion 26. When the trituration rod 40 is inserted undermost, the second rugged portion 45 is brought into contact with the second rugged portion 26.

A first rugged portion 25 is formed on an upper surface of the bottom portion 23 upward (that is, meeting the first rugged portion 44 of the trituration rod 40). The first rugged portion 25 is composed of a plurality of protrusions like the first rugged portion 44.

A flange 27 projecting in a radial direction is circumferentially provided at an upper part of the tubular body 22. A rib 28 connects the flange 27 and a lateral surface of the tubular body 22. The flange 27 and the rib 28, however, may be omitted.

A male screw member 29 is formed on a part on the lateral surface of the tubular body 22 higher than the flange 27. A female screw member 31 corresponding to the male screw member 29 is formed on the cap 30. Accordingly, the male screw member 29 is screwed into the female screw member 31 when the cap 30 is downward rotated from the top of the tubular body 22. Then, the opening 21 is closed with the cap 30, and an inner space of the tubular body 22 is sealed.

Prior to using the sample trituration vessel 20, for example, the sample trituration vessel 20 should be contained with a packing bag. In this case, it is preferable for the cap 30 to keep the sealing condition.

In use, the cap 30 is put off, and buffer 37 is poured into the tubular body 22. Then, the buffer 37 within the tubular body 22 keeps this state of being held thereby. The buffer 37 may have been poured prior to the use.

When a sample is put into the tubular body 22 and the sample is triturated, the cap 30 may be put off In this Embodiment, however, the following is available.

A notch 32 is provided protruding from a center of an upper end of the cap 30. A slit groove 33 is cut at a lower end of the notch 32, thereby making the neighborhood of the slit groove 33 weak adventurously. As illustrated with dashed lines of FIG. 2, the notch 32 can be easily cut off when the notch 32 is folded bordering on the slit groove 33. As a result, an upper part of the opening 21 is connected with the exterior. This enables to insert the sample and the trituration rod into the tubular body 22 via a hole opened by removing the notch 32 without putting the cap 30 off.

As mentioned above, the nozzle 34 is put on the cap 30 when trituration of the sample has been completed. An applying port 35 having a shape of a tapering funnel is formed at an upper part of the nozzle 34. A filter 36 for removing impurity contained in the buffer 37 is equipped with a middle part of the nozzle 34. Accordingly, when an operator puts the nozzle 34 on, turns the applying port 35 down, and squeezes the tubular body 22 with his/her hand, the buffer 37 reaches the filter 36 via the opening 21 and the hole opened by removing the notch 34. The filter 36 removes impurity, and then the buffer 37 is expelled to outside from the applying port 35.

Figure 4:
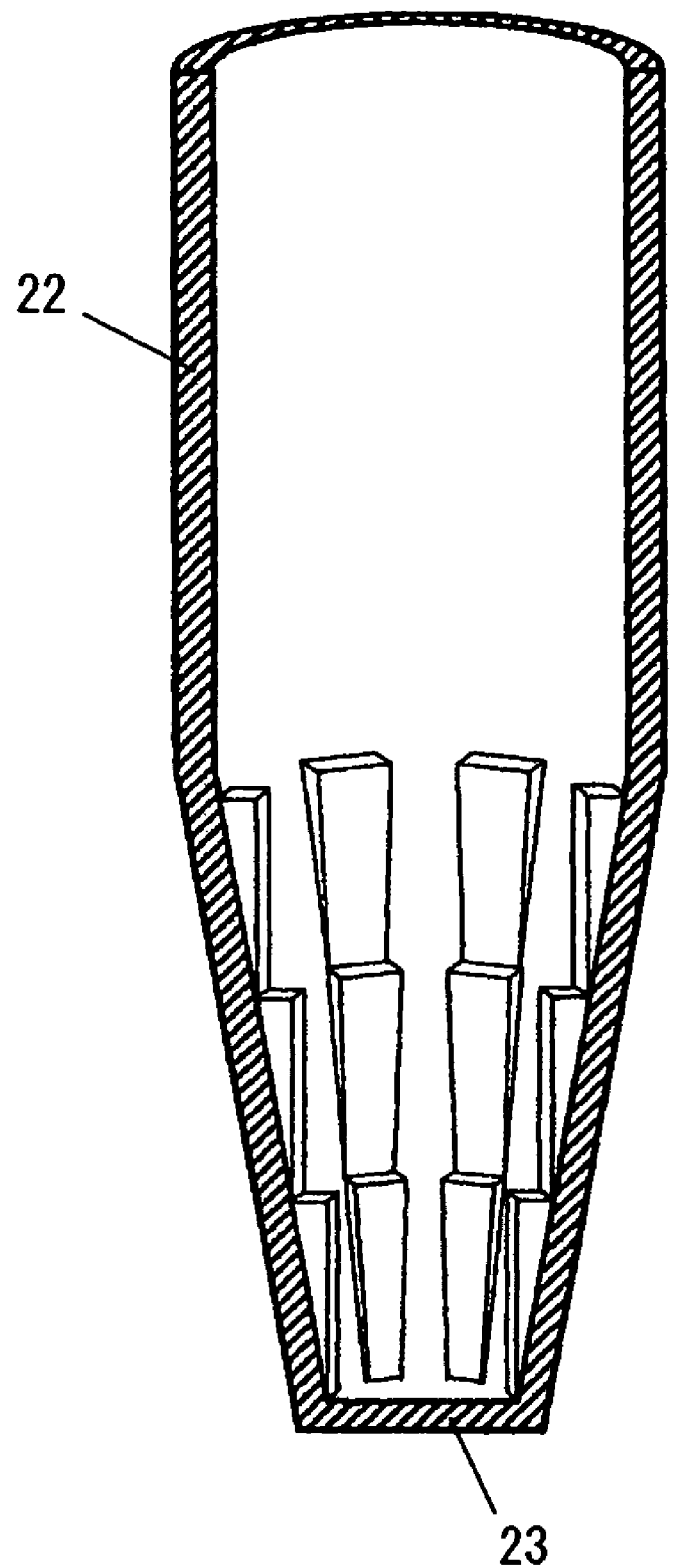
FIG. 4 is enlargement of a second rugged portion in Embodiment 2 of the present invention.

Various formation of the second rugged portion 26 is available. For example, as illustrated in FIG. 4, the second rugged portion 26 may be constituted of a rough surface having the shape of stairs. This is preferable because not only the sample can be triturated with high efficiency contacting the sample with the rough surface but also this can make it easy to release the sample trituration vessel 20 from a die when the sample trituration vessel 20 is an injection molding product made from synthetic resin.

Figure 5A:
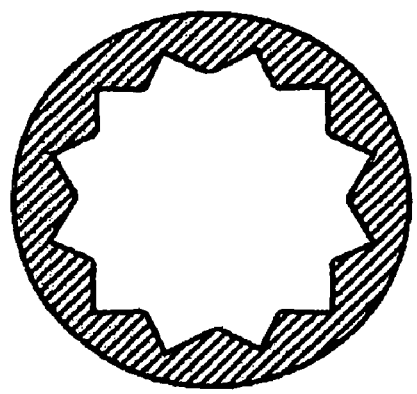
FIG. 5 (*a*) is a transverse cross section of the second rugged portion in Embodiment 2 of the present invention.
Figure 5B:
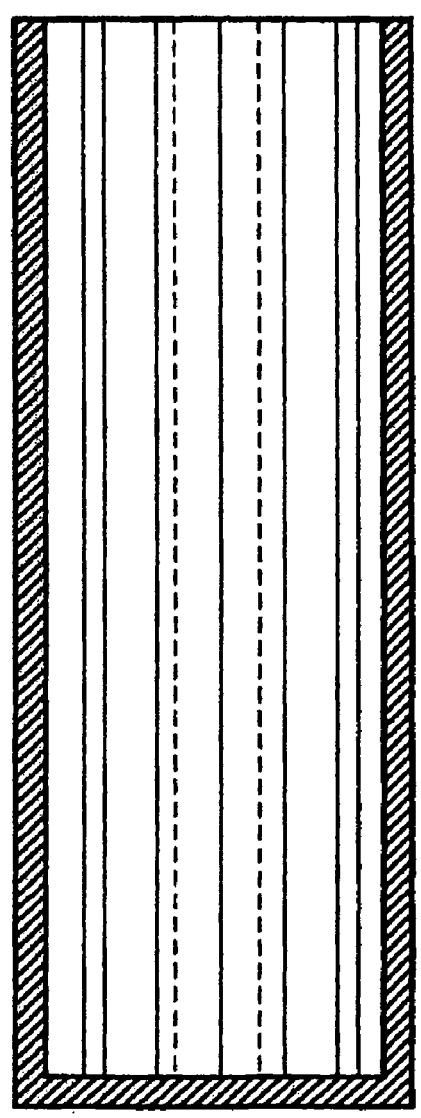

The tubular body 22 may not be tapered as described in Embodiment 1. At least a part of the internal surface of the tubular body 22 may be formed as shown in FIG. 5. These arrangements are preferable because not only the sample can be triturated with high efficiency when the sample is relatively hard but also these arrangements can make it easy to release the sample trituration vessel 20 from a die when the sample trituration vessel 20 is an injection molding product made from synthetic resin.

Herein, the tubular body 22 is formed of transparent or translucent resin (flexible material). Accordingly, as shown in FIG. 6, when an operator adds an external force to the tubular body 22 using his/her thumb 50, forefinger 51, or the like, the tubular body 22 is deformed so as to be able to break down the sample held within the tubular body 22.

This enables to triturate the buffer 37 without the trituration rod 40 in some cases. Forming the outside of the tubular body 22 rugged makes it easier to triturate the sample by means of the no slip effect thereof The tubular body 22 is transparent or translucence. The operator can see the state of buffer 37 from outside of the tubular body 22. The operator, therefore, can preferably perform trituration while adjusting pressure thereto.

Although not illustrated in FIG. 2, it is preferable to have consideration of providing a nozzle cap 38 with the applying port 35 of the nozzle 34 properly in order to prevent the buffer 37 from leaking out carelessly.

Figure 6:
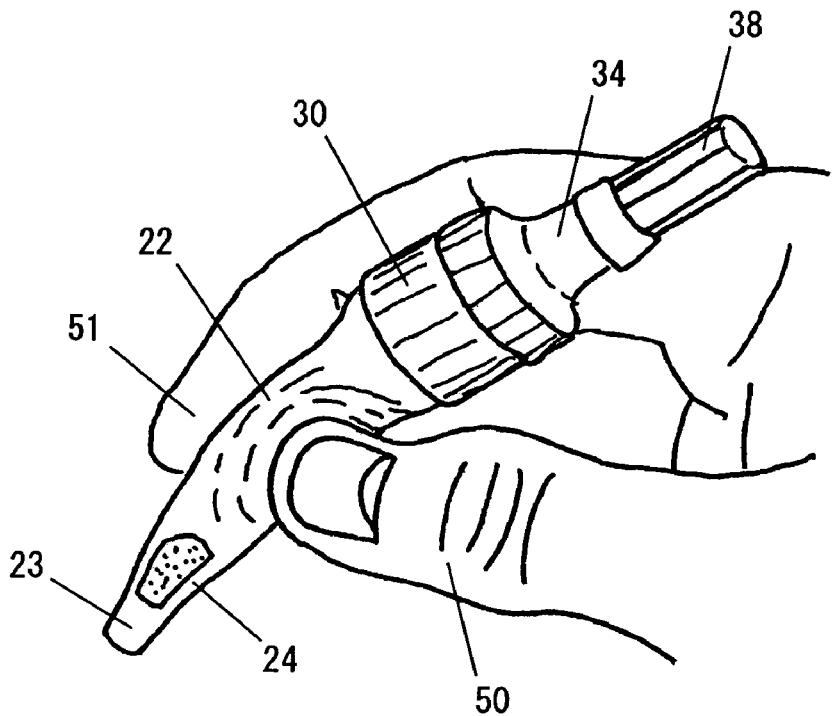
FIG. 6 is an illustration of a status of using the sample trituration vessel in Embodiment 2 of the present invention.
Figure 7:
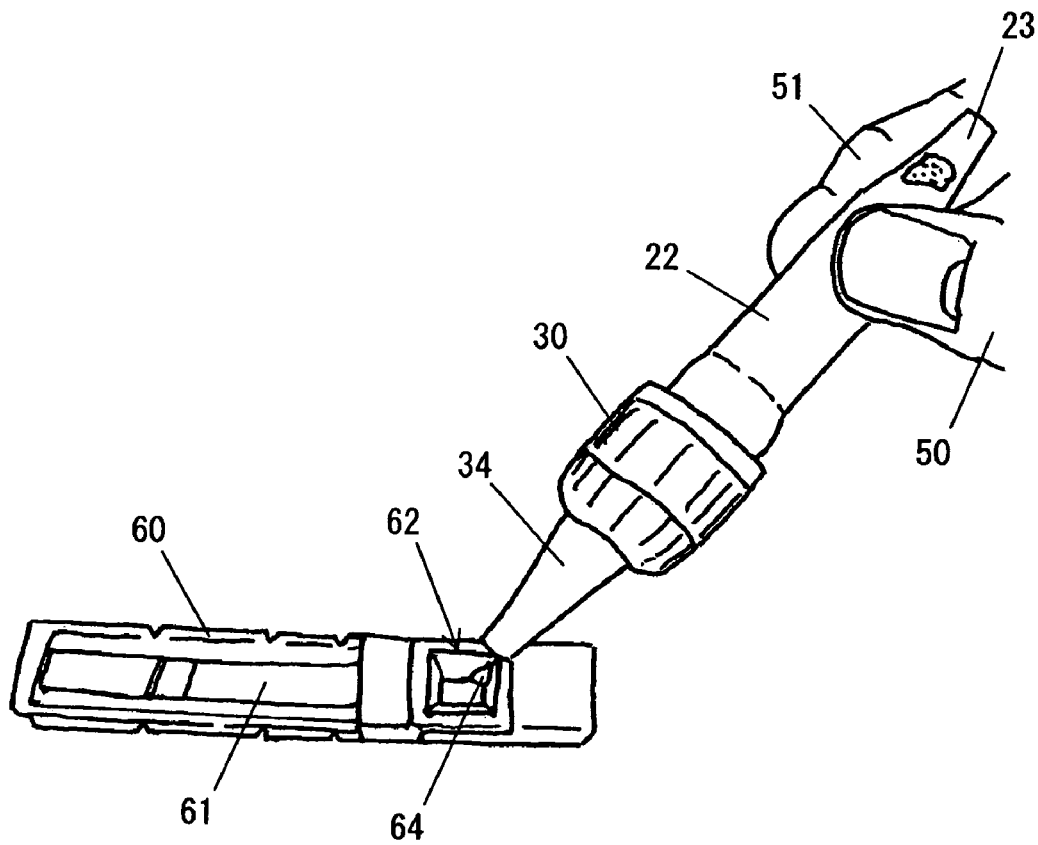
FIG. 7 is an illustration of a status of using the sample trituration vessel in Embodiment 2 of the present invention.

When the trituration has been completed in a way of a rub with fingers as shown in FIG. 6, in a way of using the trituration rod 40, or in both of them, the nozzle cap 38 is removed as illustrated in FIG. 7, and the buffer 37 filtered with the filter 36 is applied to a movable detector, which is preferable based on the immunochromatography method in view of easy and rapid operation thereof.

The detector shown in FIG. 7 comprises: a holder 60; and a test piece 61 held by the holder 60. A sample-applying part of the test piece 61 exposes to the exterior via a sample-applying port 62 made in a jig equipped with the holder 60. It is, therefore, enough for the operator to merely apply the buffer 37 filtered with the filter 36 via the sample-applying port 62.

Other points are the same as those of Embodiment 1.

Hereinafter, methods of preparing detectors used by the inventors for detecting fruit tree viruses SDV according to the immunochromatography method will be now briefly explained.

<Anti-SDV Monoclonal Antibody>

Anti-SDV monoclonal antibodies were prepared according to the method of Kohler-Milstein (Nature, 256, 495-497, 1975). Antibody-producing cells were extracted from a spleen of a mouse immunized by SDV, and then were fused with mouse myeloma cells separately prepared, thereby obtaining hybridoma cells producing anti-SDV monoclonal antibodies 4E6 and hybridoma cells producing anti-SDV monoclonal antibodies 2G2. The hybridoma cells were cultured respectively, and were injected in the abdominal cavity of a mouse, thereby obtaining ascites thereof. Ammonium sulfate fraction and protein G column purification are performed on the obtained ascites, thereby obtaining anti-SDV monoclonal antibodies 4E6 and anti-SDV monoclonal antibodies 2G2.

<Label Component>

Colloidal gold was produced according to the method of G. Frens (Nature, 241, 20-22, 1973). 40 milliliter of the anti-SDV monoclonal antibodies 2G2 are mixed to 10 microgram of colloidal gold at room temperature, thereby preparing colloidal gold (label component)-combined anti-SDV monoclonal antibodies.

<Labeled Zone>

The colloidal gold-conjugated with anti-SDV monoclonal antibodies are prepared into a condition of OD520=0.303. 36 micro liter of prepared liquid per test was applied to a glass fiber pad, and the pad was dried. Thereby, a colloidal gold-conjugated with anti-SDV monoclonal antibody-applied pad was prepared.

<Detection Zone>

0.48 micro liter of the anti-SDV monoclonal antibodies 4E6 per test was applied onto nitrocellulose membrane (Millipore Corp.: SCHF (trademark)) in the shape of lines, thereby forming a detection zone. The membrane was blocking-processed using casein solution, thereby preparing anti-SDV monoclonal antibody-turned in solid phase membrane.

<Detector>

A piece of filter paper (applying portion), the colloidal gold-conjugated with anti-SDV monoclonal antibody-applied pad, the anti-SDV monoclonal antibody-turned in solid phase membrane, and another piece of filter paper were pasted on synthetic resin with adhesive in a manner such that each end of which overlaps 3 mm, thereby producing a test piece 61. The test piece 61 was fixed on a holder 60, thereby producing a detector.

Utilizing the above detector, examples were prepared as follows:

(Example 1): a case where the sample trituration vessel 20 of Embodiment 2 was rubbed with fingers not using the trituration rod 40

(0.6 milliliter of 0.1M citric acid buffer was put into the sample trituration vessel 20, 0.06 grams of sample leaf was put into it, and trituration was performed. Then, the liquid filtered with the filter 36 was used as trituration liquid.);

(Example 2): a case where the sample trituration vessel 20 of Embodiment 2 and the trituration rod 40 were used to perform trituration (0.6 milliliter of 0.1M citric acid buffer was put into the sample trituration vessel 20, 0.06 grams of sample leaf was put into it, and trituration was performed. Then, the liquid filtered with the filter 36 was used as trituration liquid.);

(Comparative Example 1): a case where a mortar and a pestle were used to perform trituration (0.6 milliliter of 0.1M citric acid buffer was prepared, a part thereof was put into the mortar, 0.06 grams of sample leaf was put into it, and trituration was performed. Then, the other part of the 0.1M citric acid buffer was put into the mortar. The supernatant after centrifugal separation thereof was used as trituration liquid.);

(Comparative Example 2): a case of performing trituration using a flat pestle and a vessel for centrifugal separation (0.6 milliliter of 0.1M citric acid buffer was put into the vessel for centrifugal separation, 0.06 grams of sample leaf was put into it, and trituration was performed. The supernatant after centrifugal separation thereof was used as trituration liquid.);

(Comparative Example 3): a case of performing trituration using a groove-cut pestle and a vessel for centrifugal separation (0.6 milliliter of 0.1M citric acid buffer was put into the vessel for centrifugal separation, 0.06 grams of sample leaf was put into it, and trituration was performed. The supernatant after centrifugal separation thereof was used as trituration liquid.);

(Comparative Example 4): a case of performing trituration using a mesh-formed bag (0.6 milliliter of 0.1M citric acid buffer was put into the mesh-formed bag, 0.06 grams of sample leaf was put into it, and trituration was performed. The supernatant after centrifugal separation thereof was used as trituration liquid.)

Using the trituration liquid according to the respective case and 0.1M citric acid buffer, a series of dilutions (*1, *2, *4, *8, *16, *32, *64) were prepared. Only 100 micro liter thereof was applied to the applying port 62, and appearance condition of lines (herein, purplish red) derived from the colloidal gold after fifteen minutes later were observed by eyes. Comparative examples 1 to 4 are the same as described in the item of "Background Art".

Hereinafter, inflected trees 1 and 2 are orange trees inflected with fruit tree viruses SDV, and uninflected trees 1 and 2 are orange trees uninflected with fruit tree viruses SDV The result of sensitivity test with respect to these orange trees is as follows:

| | Dilution ratio of trituration liquid | | | | | | |
|---|---|---|---|---|---|---|---|
| Tree Name, Trituration | *1 | *2 | *4 | *8 | *16 | *32 | *64 |
| Inflected tree 1 | | | | | | | |
| Example 1 | + | + | + | − | | | |
| Example 2 | + | + | + | − | | | |
| Comparative example 1 | + | + | + | − | | | |
| Comparative example 2 | + | − | − | − | | | |
| Comparative example 3 | + | + | + | − | | | |
| Comparative example 4 | − | − | − | − | | | |
| Inflected tree 2 | | | | | | | |
| Example 1 | + | + | + | + | + | − | − |
| Example 2 | + | + | + | + | − | − | − |
| Comparative example 1 | + | + | + | + | − | − | − |
| Comparative example 2 | + | + | − | − | − | − | − |
| Comparative example 3 | + | + | − | − | − | − | − |
| Comparative example 4 | + | + | + | + | − | − | − |
| Uninflected tree 1 | | | | | | | |
| Example 1 | − | | | | | | |
| Example 2 | − | | | | | | |
| Comparative example 1 | − | | | | | | |
| Comparative example 2 | − | | | | | | |
| Comparative example 3 | − | | | | | | |
| Comparative example 4 | − | | | | | | |
| Uninflected tree 2 | | | | | | | |
| Example 1 | − | | | | | | |
| Example 2 | − | | | | | | |
| Comparative example 1 | − | | | | | | |
| Comparative example 2 | − | | | | | | |
| Comparative example 3 | − | | | | | | |
| Comparative example 4 | − | | | | | | |

This result indicates the following facts.

(1) Examples 1 and 2 earn detection sensitivity more than that of Comparative example 1. In addition, the usability of Examples 1 and 2 is far better than that of Comparative example 1.

(2) Comparative example 2 is inferior to any of Examples 1 and 2 and Comparative example 1 in detection sensitivity.

(3) Comparative example 3 is inferior to any of Examples 1 and 2 and Comparative example 1 in detection sensitivity when dealing with some samples.

(4) Comparative example 4 is inferior to any of Examples 1 and 2 and Comparative example 1 in detection sensitivity when dealing with some samples.

In influenza detection, the pharynx is wiped with a cotton swab to extract fluid. The cotton swab is dipped into a vessel holding buffer therein. The cotton swab is squeezed from outside of the vessel to extract fluid that has penetrated with the cotton swab to the buffer, and then detection is performed using the buffer.

The sample trituration vessel according to the present invention can be used as such a vessel. In this way, it is expected that efficiency of extracting a substance to be detected from the cotton swab is improved owing to the operation of the rugged portion.

The inventors performed model experiment (1) and experiment using samples (2) with respect to influenza detection to obtain results thereof. The results are reported as follows. The procedures of the experiment are as follows. The same buds equipped with cotton swabs at ends are prepared, and then model mucus or suction liquid from a nasal cavity, which may include a substance to be detected, are put on tips of the cotton swabs. The same composition and amount of buffer solution is applied to a first vessel (hereinafter, "Comparative example 5") that is a vessel the rugged portion 9 of which has been removed from the vessel 5 of FIG. 1, or a second vessel (hereinafter, "Example of the present invention") of the vessel 20 of FIG. 2.

Extraction process of Comparative example 5 is as follows. The cotton swab on which the model mucus or the suction liquid from the nasal cavity is put is inserted into the bottom of the first vessel, and then fingers press the first vessel from outside and rub the cotton swab five times.

Extraction process of Example of the present invention is as follows. The cotton swab on which the model mucus or the suction liquid from the nasal cavity is put is inserted into the bottom of the second vessel, and then fingers pinch the second vessel from outside and rotate the cotton bud from side to side five times.

(1) Model Experiment

In detection of influenza infection, mucus from a nasal cavity or a pharynx is used, and such mucus has considerable viscosity. Therefore, in the model experiment, blue aqueous paint is used as a model having high viscosity. That is, blue paint is put on the cotton swab, and weight thereof is measured. One milliliter of the buffer solution is used to perform the extraction process. Then, absorbance at 610 nm is measured. Theoretical absorbance (100%) is defined with absorbance where blue paint is added to one milliliter of buffer solution to dissolve fully. Measured absorbance divided by the theoretical absorbance is defined as an extraction rate (%).

Twenty times of extraction processes are performed concerning Comparative example 5 and Example of the present invention to obtain extraction rates, respectively. The results thereof are as follows.

| Frequency | Comparative example 5 (%) | Present invention (%) |
|---|---|---|
| 1 | 11.6 | 65.5 |
| 2 | 7.7 | 81.7 |
| 3 | 15.6 | 82.0 |
| 4 | 9.9 | 75.3 |
| 5 | 9.0 | 81.4 |

-continued

| Frequency | Comparative example 5 (%) | Present invention (%) |
|---|---|---|
| 6 | 11.5 | 79.9 |
| 7 | 6.6 | 73.0 |
| 8 | 6.2 | 74.6 |
| 9 | 7.9 | 92.2 |
| 10 | 6.9 | 77.3 |
| 11 | 13.1 | 72.3 |
| 12 | 8.7 | 77.0 |
| 13 | 5.6 | 68.1 |
| 14 | 8.3 | 87.1 |
| 15 | 6.9 | 59.6 |
| 16 | 5.9 | 73.2 |
| 17 | 4.5 | 83.3 |
| 18 | 4.4 | 88.3 |
| 19 | 4.7 | 92.6 |
| 20 | 9.2 | 87.1 |
| Min Value | 4.4 | 59.6 |
| Max Value | 15.6 | 92.6 |
| Ave Value | 8.2 | 78.6 |

According to Example of the present invention, extraction rates belong to a range between 59.6% and 92.6%, and 78.6% of average value is obtained. According to Comparative example 5, extraction rates belong to a range between 4.4% and 15.6%, and 8.2% of average value is obtained. That is, very higher extraction rates can be obtained according to Example of the present invention than Comparative example 5. Needless to say, the higher extraction rate is obtained, the more detection precision improves.

According to Comparative example 5, since the cotton swab is rubbed by fingers, strong power of fingers is needed. The present invention has advantage that strong power is not needed and extraction process is easy. More concretely, according to Comparative example 5, the bottom of the vessel is shaped into a cylinder whose radius is greater than that of the cotton swab, and side portion of the vessel is hard to be deformed being disturbed by the bottom face of the vessel. It is also difficult to press the cotton swab. It is thought that the sample is not solved out enough even when the operator tries to rub and soften the cotton swab. On the other hand, according to Example of the present invention, since the bottom of the vessel is tapered and the rugged portion 26 is also formed, it is thought that merely rotating the bud easily causes a sufficient amount of the sample to solve out, thereby remarkably improving the extraction ratio.

(2) Experiment Using Samples

In addition to the above-mentioned model experiment, the inventors performed experiment using samples themselves concerning Comparative example 5 and Example of the present invention, respectively. Herein, suction liquid from a nasal cavity of a flu-stricken patient was extracted with the same three cotton buds while homogenizing it well.

Moreover, four samples (samples 1 to 3 are samples of influenza A type positive, and sample 4 is a sample of influenza B type positive.) were used. Extraction buffer or the like was the same as the model experiment. The sample was prepared by diluting extracted buffer in a series of the power of two, and then measurement was performed using influenza detection kits (product made by Mizuho medy Co., LTD., trademark: Quick Chaser Flu, No. 67500).

The result is as follows. Herein, the symbol of "+" indicates positive, the symbol of "+W" indicates pseudo-positive, and the symbol of "−" indicates negative.

| Sample Ex | Original | \multicolumn{11}{c}{Dilution ratios} |
|---|---|---|---|---|---|---|---|---|---|---|---|

| Sample Ex | Original | 2 | 4 | 8 | 16 | 32 | 64 | 128 | 258 | 512 | 1024 |
|---|---|---|---|---|---|---|---|---|---|---|---|
| 1 Comparative 5 | + | + | + | + | + | +W | – | – | – | – | – |
| 1 Invention | + | + | + | + | + | + | + | + | + | +W | – |
| 2 Comparative 5 | + | + | +W | – | – | – | – | – | – | – | – |
| 2 Invention | + | + | + | + | +W | – | – | – | – | – | – |
| 3 Comparative 5 | + | + | + | +W | – | – | – | – | – | – | – |
| 3 Invention | + | + | + | + | + | +W | – | – | – | – | – |
| 4 Comparative 5 | + | – | – | – | – | – | – | – | – | – | – |
| 4 Invention | + | + | + | +W | – | – | – | – | – | – | – |

In view of the above, according to Example of the present invention, higher extraction ratio is obtained (See, Model experiment) than Comparative example 5 in any condition. It is, therefore, apparent that influenza detection sensitivity is significantly improved. In addition, Sample 1 has very high viscosity among Samples 1 to 4, and Sample 3 has high viscosity next thereto. Higher viscosity of the sample is, the higher effect the vessel according to the present invention earns.

The invention claimed is:

1. An analyte detecting set, comprising
  a sample trituration vessel for homogenizing an organic sample derived from at least one of an animal and a plant; and
  a detector,
  wherein said sample trituration vessel comprises
  a tubular body including an opening at a first end of said tubular body and a bottom part at a second end of said tubular body,
  wherein a rugged portion is disposed on an inside of said tubular body,
  wherein said tubular body is formed of flexible material, and said tubular body is configured so as to be capable of being rubbed with fingers from outside, thereby breaking the organic sample derived from at least one of the animal and the plant in said tubular body,
  wherein said detector comprises
  a test piece including a sample-applying part,
  a holder holding said test piece therein, and
  wherein said holder includes an opened sample-applying port overlapping said sample-applying part so as to expose said sample-applying part to an exterior, thereby enabling the homogenized organic sample to be applied to said sample-applying part via said sample-applying port of said holder.

2. An analyte detecting set as defined in claim 1, wherein said rugged portion is configured and arranged so as to be capable of meeting another rugged portion disposed on a trituration rod.

3. An analyte detecting set as defined in claim 1, wherein said rugged portion includes a plurality of protrusions.

4. An analyte detecting set as defined in claim 1, wherein said rugged portion is in a shape of stairs so as to constitute a rough face.

5. An analyte detecting set as defined in claim 1, wherein said rugged portion is disposed at an inner side of said bottom part.

6. An analyte detecting set as defined in claim 1, further comprising a conical tapered portion disposed adjacent said bottom part of said tubular body.

7. An analyte detecting set as defined in claim 6, wherein said rugged portion is disposed at an inner side of said tapered portion.

8. An analyte detecting set as defined in claim 1, wherein said tubular portion is formed of transparent or translucent material.

9. An analyte detecting set as defined in claim 1 further comprising:
  a trituration rod configured to be inserted into said sample trituration vessel and further configured to triturate the sample held within said sample trituration vessel,
  wherein said trituration rod comprises:
  a rod body; and
  a head portion disposed at an apical end of said rod body, and
  wherein another rugged portion that is configured and arranged to meet the rugged portion of said sample trituration vessel is disposed at said head portion.

10. An analyte detecting method, comprising:
  putting a sample into the sample triturating vessel as defined in claim 9;
  triturating the sample using the triturating rod and the sample triturating vessel;
  applying the triturated sample to the sample-applying part of the test piece; and
  obtaining a detection result using the detector.

11. An analyte detecting method, comprising:
  putting a sample into the sample triturating vessel as defined in claim 1;
  rubbing the tubular body with fingers, thereby triturating the sample;
  applying the triturated sample to the sample-applying part of the test piece; and
  obtaining a detection result using the detector.

* * * * *